US012611336B2

(12) United States Patent
Maschino et al.

(10) Patent No.:  US 12,611,336 B2
(45) Date of Patent:         Apr. 28, 2026

(54) HYDRO-ENLARGED, APERTURED NON-WOVEN WEB AND METHOD OF MAKING SAME

(71) Applicant: FITESA FILM PRODUCTS LLC, Simpsonville, SC (US)

(72) Inventors: Andrew D. Maschino, Paris, IL (US); Michael Estel Fisher, Rosedale, IN (US); Jesse B. Schalburg, Terre Haute, IN (US); John Richard Renner, Marshall, IL (US)

(73) Assignee: FITESA FILM PRODUCTS LLC, Simpsonville, SC (US)

( * ) Notice: Subject to any disclaimer, the term of this patent is extended or adjusted under 35 U.S.C. 154(b) by 648 days.

(21) Appl. No.: 17/893,730

(22) Filed: Aug. 23, 2022

(65) Prior Publication Data

US 2023/0077122 A1      Mar. 9, 2023

Related U.S. Application Data

(60) Provisional application No. 63/313,516, filed on Feb. 24, 2022, provisional application No. 63/241,794, filed on Sep. 8, 2021.

(51) Int. Cl.
*A61F 13/15*          (2006.01)
*A61F 13/512*          (2006.01)

(52) U.S. Cl.
CPC ...... *A61F 13/15731* (2013.01); *A61F 13/512* (2013.01); *A61F 2013/15373* (2013.01);
(Continued)

(58) Field of Classification Search
CPC .............. A61F 13/15731; A61F 13/512; A61F 2013/15373; A61F 2013/15715; A61F 2013/15861; A61F 2013/15934
See application file for complete search history.

(56) References Cited

U.S. PATENT DOCUMENTS

| | | | |
|---|---|---|---|
| 2008/0311815 A1* | 12/2008 | Gupta | D21H 13/20 |
| | | | 162/146 |
| 2018/0044826 A1* | 2/2018 | Maschino | B29C 48/002 |
| 2020/0330292 A1 | 10/2020 | Maschino et al. | |

FOREIGN PATENT DOCUMENTS

WO          2018136925 A1      7/2018

OTHER PUBLICATIONS

International Preliminary Report on Patentability dated Mar. 5, 2024, for International Patent Application No. PCT/US2022/041226.

(Continued)

*Primary Examiner* — Jacqueline F Stephens
(74) *Attorney, Agent, or Firm* — KARCESKI IP LAW, PLLC

(57) ABSTRACT

A hydro-enlarged apertured non-woven web includes a plurality of fibers with a plurality of bond points, a first surface defining a planar top, and a second surface defining a planar bottom. The second surface is separated from the first surface by a first distance defining a loft. A plurality of apertures extending through the non-woven web. The plurality of apertures is formed by spraying a fluid against an unapertured precursor web, causing a plurality of pins disposed on a pinned roller to punch through the unapertured precursor web. The unapertured precursor web has a third surface defining a planar top and a fourth surface defining a planar bottom, where the third surface is separated from the fourth surface by a second distance defining a precursor loft. The loft is greater than the precursor loft by a loft increase within a range of 50-110%.

21 Claims, 9 Drawing Sheets

(52) U.S. Cl.
CPC ............... *A61F 2013/15715* (2013.01); *A61F 2013/15861* (2013.01); *A61F 2013/15934* (2013.01)

(56) References Cited

OTHER PUBLICATIONS

International Search Report and Written Opinion dated Jan. 3, 2023, for International Patent Application No. PCT/US2022/041226.

\* cited by examiner

1

HYDRO-ENLARGED, APERTURED NON-WOVEN WEB AND METHOD OF MAKING SAME

CROSS-REFERENCE TO RELATED APPLICATION(S)

This patent application relies for priority on U.S. Provisional Patent Application Ser. No. 63/241,794, filed on Sep. 8, 2021, and on U.S. Provisional Patent Application Ser. No. 63/313,516, filed on Feb. 24, 2022, the entire contents of both of which are incorporated herein by reference.

FIELD OF THE INVENTION

The present invention concerns a hydro-enlarged, apertured non-woven web that may be employed, in one non-limiting environment, as a top sheet in a disposable, wearable article such as a diaper, adult incontinence garment, or feminine hygiene product. The present invention also encompasses a method of making a hydro-enlarged, apertured non-woven web.

DESCRIPTION OF THE RELATED ART

As should be apparent to those skilled in the art, there are numerous techniques in the art for creating an apertured non-woven material.

Typically, to create a conventional, apertured non-woven, a unapertured non-woven web is mechanically pierced by a plurality of hot pins. The hot pins effectively push through the unapertured non-woven web to create a plurality of holes therethrough.

One downside, among others, with conventional, hot pin punched, non-woven web is that the temperature of the pins and rolls employed in the hot pin aperturing process may be higher than the melting point of the nonwoven fibers and, thus, tend to melt the fibers in the non-woven web in the immediate vicinity of the apertures that the hot pins create. Once cooled, the melted fibers coalesce into hard rings around the apertures. These hard rings are tactilely unsatisfactory. Moreover, they present an unappealing visual appearance to the hot pinned, apertured non-woven web.

Among other objectives, the present invention seeks to avoid the creation of these hard rings.

Separately, it is noted that hot pin punching does not alter the loft, or thickness, of the non-woven web, although there may be some minor distortions created at the locations of the hard rings resulting from the pushing of the pins through the non-woven web.

The present invention seeks to create an apertured non-woven web with a higher loft than apertured non-woven web created via the hot pin approach.

Still further advantages and features of the present invention will be made apparent by the discussion presented hereinbelow.

SUMMARY OF THE INVENTION

The present invention seeks to address one or more of the deficiencies in the prior art.

Without limiting the present invention, the present invention seeks to create an apertured non-woven web having a lower bulk density after processing than the bulk density of a material prior to processing. A material with a lower bulk density is one where the (mass/area) $gm/m^2$ parameter of the material (also referred to as the "basis weight") remains constant from the beginning to the end of the process. However, the mass/volume ($gm/m^3$) parameter (also referred to as the "bulk") is lower at the end of the process than at the start of the process, because the loft of the material is increased.

In particular, the present invention provides a hydro-enlarged apertured non-woven web that includes a plurality of fibers, a plurality of bond points securing the plurality of fibers to one another to define a non-woven web, a first surface defining a planar top to the non-woven web, and a second surface defining a planar bottom to the non-woven web. The second surface is separated from the first surface by a first distance defining a loft. A plurality of apertures extends through the non-woven web from the first surface to the second surface. The plurality of apertures is formed by spraying a fluid against an unapertured precursor web, causing a plurality of pins disposed on a pinned roller to punch through the unapertured precursor web. The unapertured precursor web has a third surface defining a planar top and a fourth surface defining a planar bottom. The third surface is separated from the fourth surface by a second distance defining a precursor loft. The loft is greater than the precursor loft by a loft increase within a range of 50-110%. Here, the temperature of the fluid and the temperature of the pinned roller is maintained at a temperature lower than the melting point of the fibers.

In one contemplated embodiment, the non-woven web has a basis weight in a range of 8-100 gsm. Alternatively, the non-woven web has a basis weight in a range of 10-60 gsm. Still further, it is contemplated that the non-woven web has a basis weight of one of 10 gsm, 20 gsm, 25 gsm, or 50 gsm.

In other embodiments, the loft of the hydro-enlarged apertured non-woven web is in a range of 150-1000 microns or in a range of 200-900 microns. Still further, it is contemplated that the loft may be at least one of 200, 325, 450, or 875 microns.

For the present invention, it is contemplated that the precursor loft is in a range of 50-600 microns, in a range of 100-500 microns, or one of 100, 131, 200, 225, or 500 microns.

For the hydro-enlarged apertured non-woven web of the present invention, the loft increase is contemplated to fall within a range of 60-90% or within a range of 70-80%.

In an embodiment of the hydro-enlarged apertured non-woven web of the present invention incorporating materials including polylactic acid or polyactide ("PLA"), the loft increase is contemplated to fall within a range of 40-70% or within a range of 50-60%.

The present invention also encompasses a method of manufacturing a hydro-enlarged apertured non-woven web. The method includes introducing an unapertured non-woven precursor web to a pinned roller comprising a surface on which a plurality pins are disposed, where the unapertured non-woven precursor web comprises a plurality of fibers secured to one another at a plurality of bond points, and where the unapertured non-woven precursor web has a first surface defining a planar top and a second surface defining a planar bottom. The second surface is separated from the first surface by a first distance defining a precursor loft. Pressurized fluid is sprayed against the first surface, thereby causing a plurality of pins disposed on a pinned roller to punch through the unapertured non-woven precursor web to create a plurality of apertures therethrough, resulting in the hydro-enlarged apertured non-woven web. The hydro-enlarged apertured non-woven web has a third surface defining a planar top and a fourth surface defining a planar bottom. The third surface is separated from the fourth surface by a second distance defining a loft. The spraying causes the loft to be greater than the precursor loft. Specifically, the loft is greater than the precursor loft by a loft increase within a range of 50-110%. Here again, the temperature of the fluid and the temperature of the pinned roller is maintained at a temperature lower than the melting point of the fibers.

In various embodiments, it is contemplated that the pressurized fluid is pressurized within a range from 250-650 psi (1723.7-4481.6 kPa), pressurized within a range from 400-550 psi (2757.9-3792.1 kPa), or pressurized to one of 300 psi (2068.4 kPa), 400 psi (2757.9 kPa), 450 psi (3102.6 kPa), 500 psi (3447.4 kPa), or 585 psi (4033.4 kPa).

Still further, embodiments of the present invention contemplate that the pressurized fluid is maintained at a temperature within a range of 75-170° F. (23.89-76.67° C.), that the pressurized fluid is maintained at a temperature within a range of 100-170° F. (37.78-76.67° C.), or that the pressurized fluid maintained at a temperature of one of 101° F. (38.33° C.), 115° F. (46.11° C.), 116° F. (46.67° C.), 125° F. (51.67° C.), or 160° F. (71.11° C.).

The present invention also contemplates that the method will result in a loft increase (for polymer materials) that is within a range of 60-90% or within a range of 70-80%. For materials including polylactic acid or polylactide ("PLA"), the loft increase is contemplated to be within a range of 40-70% or within a range of 50-60%.

Still other aspects and features of the present invention will be made apparent from the description that follows.

BRIEF DESCRIPTION OF THE DRAWINGS

The present invention will now be described in connection with the drawings appended hereto, in which.

BRIEF DESCRIPTION OF EMBODIMENT(S) OF THE INVENTION

The present invention will now be described in connection with one or more embodiments. Where possible, the same reference numbers are employed to refer to like structures and/or features. Unless otherwise indicated, the use of the same reference numbers should not be understood to mean that each structure using the same reference number is identical to each other structure using that reference number. To the contrary, as should be apparent to those skilled in the art, variations and equivalents of the structures may be employed. Those variations and equivalents are contemplated to be encompassed by the present invention, even if not explicitly discussed herein.

The present invention also will be described in connection with one or more materials. Any materials described herein are intended to be exemplary of the possible materials that may be employed and are not intended to limit the scope of the present invention. Moreover, any discussion about specific characteristics and parameters of any material should not be understood to be limiting of the material, unless otherwise stated.

Figure 1:
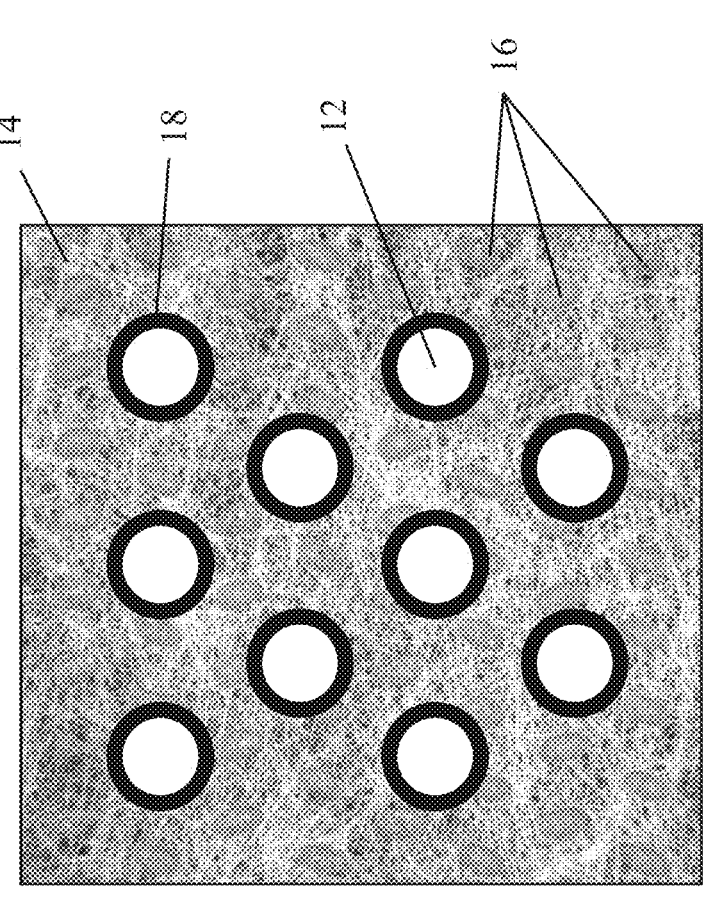
FIG. 1 is a graphical top view of an unapertured non-woven web that has been hot pin punched according to conventional techniques.

FIG. 1 is a graphical representation of a hot pin apertured non-woven web 10, which was created using a hot pin puncturing technique known to those skilled in the art.

To create the hot pin apertured non-woven web 10 via hot pin punching, an unapertured non-woven web is fed into a hot pin puncher.

The hot pin puncher typically includes two counter-rotating rollers. The surface of the first roller of the two rollers includes a plurality of heated pins disposed on thereon. The second roller of the two rollers includes a plurality of wells that are in register with the heated pins. As the first and second rollers counter-rotate, the pins from the first roller fit into the wells in the second roller.

By way of background, the heated pins may be made from metal or any other suitable material that may be heated. The second roller may be coated with a rubber material, for example.

As the unapertured non-woven web passes between the first and second rollers, the heated pins pierce (or are pushed through) the unapertured non-woven web. During this process, the heated pins perforate the unapertured non-woven web and create a plurality of apertures 12 through the unapertured non-woven web to create the hot pin apertured non-woven web 10.

The unapertured non-woven web is made from a plurality of fibers 14 that are connected to one another via a plurality of bond points 16. The bond points 16 may be created via ultrasonic welding, thermal bonding, pressure, mechanical deformation, adhesives, and the like during the manufacture of the unapertured non-woven web. The construction of the unapertured non-woven web is well known to those skilled in the art and, therefore, further elaboration is not provided here.

When the unapertured non-woven web passes through the hot pin puncher, the fibers 14 in contact with the surface of the heated pin are pushed together. One undesirable result of contact between the fibers 14 and the heated pins is that the fibers 14 melt. As a result, after the hot pin apertured non-woven web 10 is released from the heated pins, the molten fibers 14 resolidify. When the fibers 14 resolidify, they form rings 18 around the newly formed apertures 12.

As should be apparent to those skilled in the art, the rings 18 are small, hard structures that are created in the hot pin apertured non-woven web 10.

Apertured non-woven webs commonly are employed as top sheets for disposable, wearable articles such as a diapers, adult incontinence garments, and/or feminine hygiene products, among other products. As the name suggests, a top sheet is the topmost sheet in the disposable, wearable article. Specifically, the top sheet is the layer that comes into contact with the user's skin. As a result, the top sheet is visible to the user of the disposable, wearable article. The top sheet also is tactilely perceptible by the user, because the top sheet contacts the user's skin.

As should be apparent to those skilled in the art, there are several features that are desirable for a top sheet. First, users prefer for the top sheet to have a soft look. Second, users prefer for the top sheet to be fluffy, which means that users prefer for the top sheet to have a soft, tactile feel. Third, the top sheet is expected to conduct fluids and insults to the absorbent core as quickly as possible so that the user does not experience discomfort resulting from fluids that linger against the user's skin. Therefore, it is desirable for the fibers in the top sheet to be sufficiently separated from one another to assist with conveyance of the fluid to the absorbent core. In addition, apertures are added to the top sheet to further assist the passage of fluids to the absorbent core by creating passageways for the fluid through the top sheet to the absorbent core therebeneath.

It is noted that, while the present invention is discussed for use as a top sheet, the present invention should not be understood to be limited solely as a top sheet. To the contrary, the desirable qualities enumerated hereinabove also may find application in other aspects of a disposable, wearable article. For example, the hydro-enlarged apertured non-woven web 20 of the present invention may be used as an acquisition distribution layer ("ADL"), back sheet, or other component of a disposable, wearable article, as may be required or desired.

Returning to the hot pin apertured non-woven web 10 illustrated in FIG. 1, the rings 18 may be visible to the naked eye. This is undesirable, because users of disposable, wearable articles prefer that the top sheet have a soft appearance.

A top sheet that presents a plurality of hard rings 18 is not one that a user would consider to be "soft looking."

Still further, the rings 18 also are tactilely perceptible. In other words, a user can feel the rings 18 on the hot pin apertured non-woven web 10 when drawing his or her fingers thereacross. Again, this is undesirable, because users prefer a top sheet with a soft feel. The hard rings 18 do not contribute to a soft feel.

In addition, the hard rings 18 may leave temporary marks on a person's skin after prolonged contact with the user's skin. While not harmful to the user or damaging to the user's skin, the temporary marks may be concerning to a user, because they may resemble a rash or other skin irritation. This adds to the undesirable nature of the hot pin apertured non-woven web 10. Separately, it is noted that loft (or thickness) of the top sheet is a variable that also contributes to the softness of the web. As a general rule, the greater the loft of the top sheet (i.e., the greater the thickness of the top sheet), the softer the look and feel associated with the top sheet, because the fibers 14 are separated from one another to a greater extent. As should be apparent to those skilled in the art, loft alone is not a definitive parameter for softness, because a thick, dense top sheet would not necessarily have a soft feel. Nonetheless, for purposes of the present invention, loft is a variable that may be employed to help define the softness of the top sheet as explained in greater detail hereinbelow.

In the prior art, when piercing a unapertured non-woven web with a hot pin to create a hot pin apertured non-woven web, it is understood that the loft of the hot pin apertured non-woven web 10 will be the same as the loft of the unapertured non-woven web before being processed through the hot pin puncher. As should be apparent to those skilled in the art, the process of hot pin aperturing of the unapertured non-woven web to create the hot pin apertured non-woven web 10 does not cause the loft of the web to increase, because the web is merely pierced by the plurality of hot pins. The positions of the fibers 14 in the thickness direction (in the direction of the loft of the web) are not otherwise altered by the hot pin punching process.

The present invention encompasses a hydro-enlarged apertured non-woven web 20 and a method for making the hydro-enlarged apertured non-woven web 20.

There are at least two aspects of the hydro-enlarged apertured non-woven web 20 of the present invention that are notable. First, the hydro-enlarged apertured non-woven web 20 includes apertures 44, but does not include any of the hard rings 18 identified with respect to the hot pin apertured non-woven web 10 known in the prior art. The absence of the hard rings 18 not only improves the visual appeal of the hydro-enlarged apertured non-woven web 20, but it also improves the tactile feel of the hydro-enlarged apertured non-woven web 20. Specifically, the hydro-enlarged apertured non-woven web 20 is softer, both in appearance and texture, when compared to the hot pin apertured non-woven web 10 known in the prior art. Second, the loft of the hydro-enlarged apertured non-woven web 20 is greater than the unapertured non-woven precursor web 22. The increased loft also improves the visual and tactile properties of the hydro-enlarged apertured non-woven web 20, as compared to the prior art.

For the present invention, it is also proffered that, instead of considering loft alone, the bulk of the hydro-enlarged apertured non-woven web 20 may be considered. "Bulk" refers to the parameter of the mass/volume $(gm/m^3)$ of the material. Since the (mass/area) $gm/m^2$ parameter of the material (also referred to as "basis weight") remains constant from the beginning to the end of the process, when the loft increases, the bulk (the mass/volume (gm/m³) parameter) decreases. As such, the bulk of the material is dependent on the basis weight of the material. For this reason, in the discussion that follows, the loft is discussed with respect to the hydro-enlarged apertured non-woven web 20. The discussion of loft also is intended to address the bulk of the material.

Figure 2:
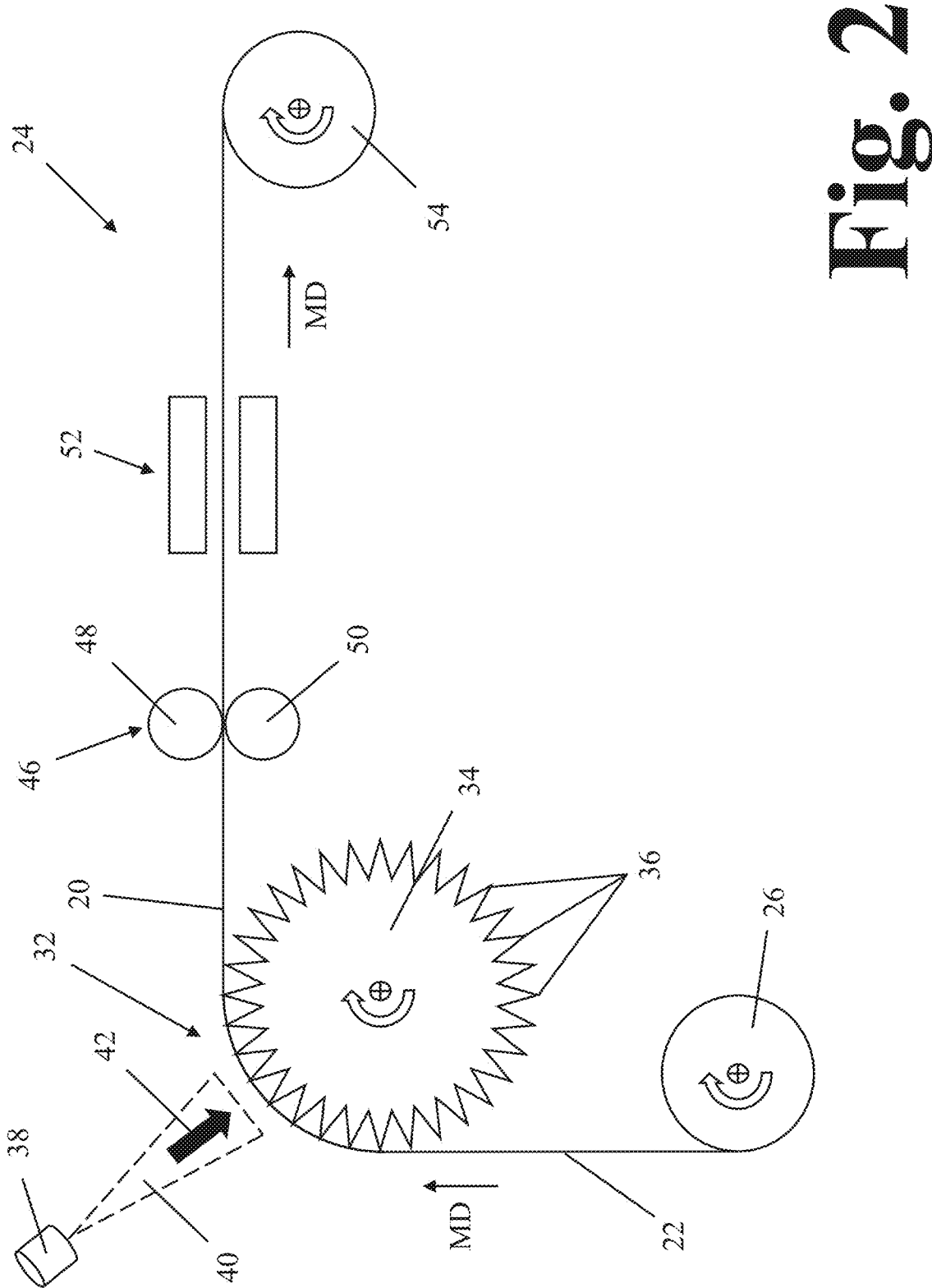
FIG. 2 is a graphical representation of one contemplated embodiment of an apparatus that may be used to manufacture the hydro-enlarged apertured non-woven web of the present invention.

The hydro-enlarged apertured non-woven web 20 may be manufactured via an apparatus, such as the hydro-enlarging apparatus 24 illustrated in FIG. 2.

The hydro-enlarging apparatus 24 includes a first roller 26 from which the unapertured non-woven precursor web 22 is unspooled. The unapertured non-woven precursor web 22 is a non-woven web constructed according to conventional techniques.

The unapertured non-woven precursor web 22 is not illustrated herein, because the construction of the unapertured non-woven precursor web 22 is known to those skilled in the art. However, the following features are identified in connection with FIG. 3, which provides an enlarged micrographic view one embodiment of the hydro-enlarged apertured non-woven web 20 of the present invention.

The unapertured non-woven precursor web 22 comprises a plurality of fibers 28 that are connected to one another at a plurality of bond points 30. The bond points 30 define locations where the fibers 28 are connected to one another via ultrasonic welding, thermal bonding, pressure bonding, and/or adhesives, for example. The bond points 30 maintain the integrity of the unapertured non-woven precursor web 22 by preventing the fibers 28 from separating from one another. Alternatively, the bond points 30 may be omitted without departing from the scope of the present invention.

As used herein, the term "non-woven web," which includes the unapertured non-woven precursor web 22 and the hydro-enlarged apertured non-woven web 20, is used in its generic sense to define a generally planar structure that is relatively flat, flexible, and porous, and includes staple fibers 28 or continuous fibers or filaments 28. The non-woven web may be the product of any process for forming the same, such as a non-woven spunbond and melt blown non-woven webs. The non-woven web may include a composite, a combination of webs, or a composite of one or more film(s) and non-woven web(s). The non-woven web may comprise any polymeric material from which a fiber can be produced and/or may comprise cotton or other natural fibers. In an embodiment, the non-woven web may be a spunbond material, made of polypropylene fibers, polyethylene fibers, and the like. Fibers that comprise different polymers may also be blended. In an embodiment, the fibers may be so-called bi-component ("bi-co") fibers that comprise a core of one material and a sheath of another material. Polymers are contemplated to encompass, but not be limited to, polyethylene, polypropylene, elastomers, polyesters, rayon, cellulose, nylon, and blends thereof.

The unapertured non-woven precursor web 22 is contemplated to be any type of non-woven web as discussed hereinabove. The unapertured non-woven precursor web 22 also is contemplated to have a basis weight of from 8 to 100 gsm (grams per square meter). Without limiting the present invention, any basis weight from 8 to 100 gsm may be employed. This includes, without limitation, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 gsm.

With renewed reference to FIG. 2, from the first roller 26, the unapertured non-woven precursor web 22 is conveyed, under tension, to a hydro-enlarging station 32, as illustrated in FIG. 2. The direction of travel of the unapertured non-woven precursor web 22 is the machine direction MD, as illustrated. For clarity, it is noted that the cross-direction, which is across the width of the unapertured non-woven precursor web 22, is the transverse direction TD. The transverse direction TD is orthogonal to the machine direction MD, as should be apparent to those skilled in the art. The transverse direction TD defines, in part, the width of the non-woven web passing through the hydro-enlarging apparatus 24.

The hydro-enlarging station 32 includes a pinned roller 34 with a plurality of pins 36 disposed on its surface. In one contemplated embodiment, the pins 36 are separated from one another so that there is a space or "valley" between adjacent pins. In another contemplated embodiment, one or more of the pins 36 are in contact with one or more adjacent pins 36, as required or as desired. In other words, the spacing of the pins 36 from one another may be varied without departing from the scope of the present invention.

The hydro-enlarging station 32 also includes a plurality of fluid jets 38. The fluid jets 38 direct a pressurized stream 40 of a fluid, such as water droplets, onto the unapertured non-woven precursor web 22 to press the unapertured non-woven precursor web 22 against the pins 36 on the pinned roller 34. The direction of flow of the pressurized stream 40 is indicated by the arrow 42.

For purposes of the present invention, the fluid is contemplated to be water, but the fluid is not limited to water. "Water" includes pure water and solutions made with water. A water solution is contemplated to include water as the solvent and solutes that include, but are not limited to, surfactants, disinfectants, antimicrobial agents, antiviral agents, antifungal agents, stabilizers, colorants, detergents, and the like. In the discussion that follows, any reference to "water" is intended to encompass fluids including solutions, as noted hereinabove, unless otherwise specified.

In FIG. 2, only one of the fluid jets 38 is visible. It is noted that the hydro-enlarging station 32 is contemplated to include a plurality of fluid jets 38 disposed across the full width of the hydro-enlarging station 32 and the unapertured non-woven precursor web 22 in the transverse direction TD. It is contemplated that the pressurized streams 40 from the fluid jets 38 overlap one another in the transverse direction TD so that the pressurized water/fluid droplets are applied uniformly across the full width of the unapertured non-woven precursor web 22 in the transverse direction TD.

It is noted that the pressurized streams 40 do not need to overlap to remain within the scope of the present invention. Moreover, it is also contemplated that, in areas where the pressurized streams 40 do not overlap, apertures 44 may not be formed.

It is also contemplated that the pressurized stream 40 will be applied to the unapertured non-woven precursor web 22 at a predetermined pressure and predetermined temperature. The predetermined pressure and predetermined temperature employed are anticipated to be varied depending on the basis weight of the unapertured non-woven web precursor 22 and the degree to which the loft (discussed in connection with FIG. 4, below) is to be increased.

When the unapertured non-woven precursor web 22 is subjected to the pressurized stream 40, the unapertured non-woven precursor web 22 is pressed against the pins 36 on the surface of the pinned roller 34. The pressurized stream 40 causes the pins 36 to pierce or punch through the unapertured non-woven precursor web 22, thereby creating the plurality of apertures 44 in the unapertured non-woven precursor web 22. In this manner, the hydro-enlarged apertured non-woven web 20 is created.

It is noted that the basis weight of the hydro-enlarged apertured non-woven web 20 will be the same as the unapertured non-woven precursor web 22, because no material is added to the unapertured non-woven precursor web 22 during the hydro-enlarging process. Therefore, the basis weight is not altered. As a result, the hydro-enlarged apertured non-woven web 20 is contemplated to have a basis weight of from 8 to 100 gsm (grams per square meter). Without limiting the present invention, the hydro-enlarged apertured non-woven web 20 may have any specific basis weight from 8 to 100 gsm, consistent with the discussion above. This includes, without limitation, 8, 9, 10, 11, 12, 13, 14, 15, 16, 17, 18, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 gsm. In other contemplated embodiments, the basis weight is contemplated to fall within a range of 10-60 gsm, with basis weights of 10 gsm, 20 gsm, 25 gsm, and 50 gsm being identified as specific examples consistent with the present invention.

It is possible that the fluid may deposit a coating onto the fibers 28 in the unapertured non-woven precursor web 22. For example, a surfactant may be added to the fibers 28. If so, the basis weight may increase, but not to an appreciable amount, as should be apparent to those skilled in the art. At least for this reason, the hydro-enlarged apertured non-woven web 20 is considered to have the same basis weight as the unapertured non-woven precursor web 22.

Figure 3:
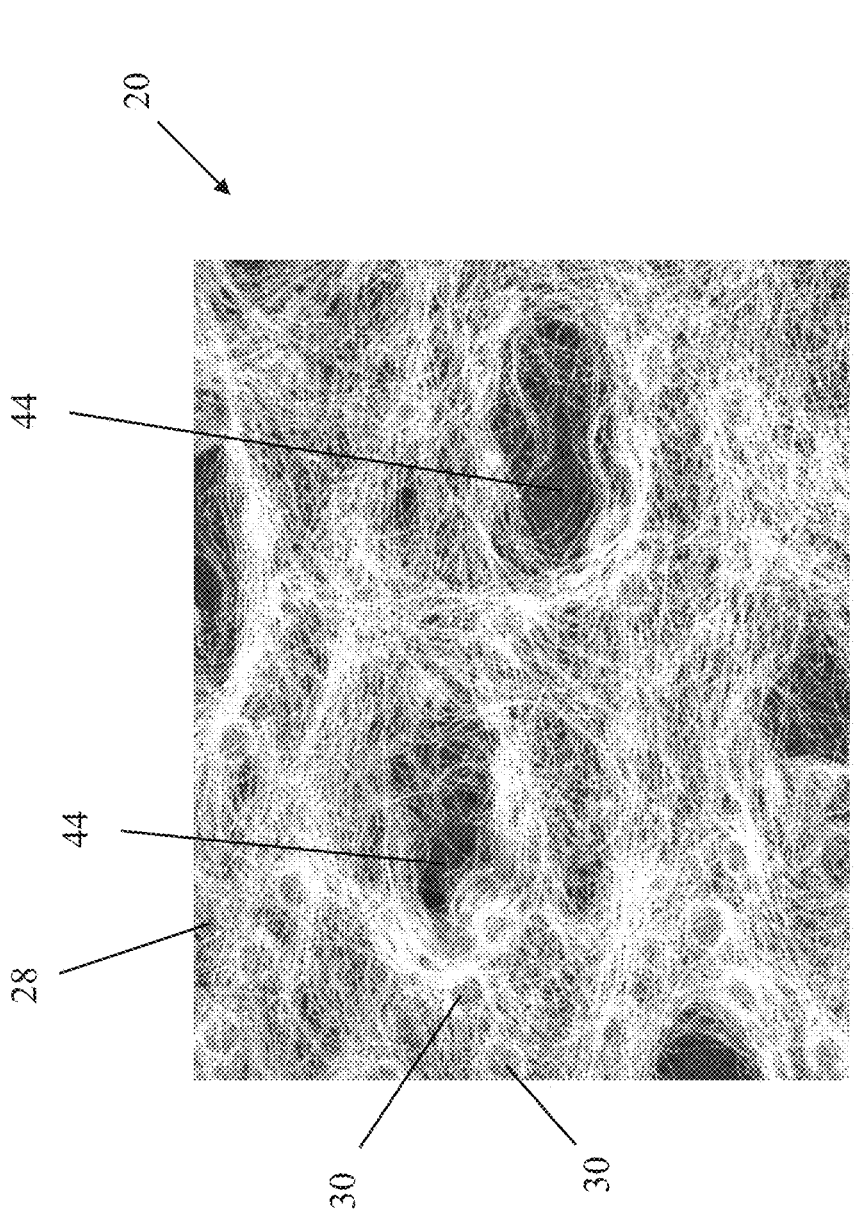
FIG. 3 is an expanded, top view of one example of the hydro-enlarged apertured non-woven web manufactured using the apparatus illustrated in FIG. 2.

FIG. 3 is an enlarged micrograph of one embodiment of the hydro-enlarged apertured non-woven web 20 of the present invention, showing several of the apertures 44 in the hydro-enlarged apertured non-woven web 20.

With renewed reference to FIG. 2, the hydro-enlarged apertured non-woven web 20 proceeds, under tension, from the hydro-enlarging station 32 to an optional, dewatering station 46. The dewatering station 46 includes a first dewatering roller 48 and a second dewatering roller 50 that counter-rotate. The first and second dewatering rollers 48, 50 squeeze the hydro-enlarged apertured non-woven web 20 to remove water (or other fluid) retained therein after the hydro-enlarging station 32. The pressure applied by the first and second dewatering rollers 48, 50 is chosen to avoid altering the final loft L2 of the hydro-enlarged apertured non-woven web 20.

From the dewatering station 46, the hydro-enlarged apertured non-woven web 20 proceeds, under tension, to an optional dryer 52. At the dryer 52, any remaining water/fluid is removed so that the hydro-enlarged apertured non-woven web 20 may be collected onto a second, final roller 54.

The dryer 52 may be any type known to those skilled in the art. It is contemplated that the dryer 52 will apply air pressure or a vacuum to the hydro-enlarged apertured non-woven web 20 to remove water/fluid remaining in the fibers 28. It is also contemplated that heat may be employed at the dryer 52, as appropriate.

While FIG. 2 illustrates the hydro-enlarging apparatus 24 with a first roller 26, a hydro-enlarging station 32, a dewatering station 46, a dryer 52, and a second roller 54, the present invention should not be understood to be limited solely to this arrangement. It is contemplated that the hydro-enlarging apparatus 24 may have a larger or a fewer number of components, as required or as desired. For example, the hydro-enlarging apparatus 24 may follow immediately after one or more stations that are employed to create the unapertured non-woven precursor web 22. Still further, rather than being gathered on a final roller 54, the hydro-enlarged apertured non-woven web 20 may be subjected to further processing stations including, but not limited to a station where a surfactant may be applied to the hydro-enlarged apertured non-woven web 20. In another contemplated variation, for example, an embosser (not shown) may be included to impress one or more surface ornamentations onto the hydro-enlarged apertured non-woven web 20. In an alternative embodiment, instead of unwinding the unapertured non-woven precursor web 22 from the first roller 26, the hydro-enlarging apparatus 24 may be in line with an apparatus that manufactures the unapertured non-woven precursor web 22.

Figure 4:
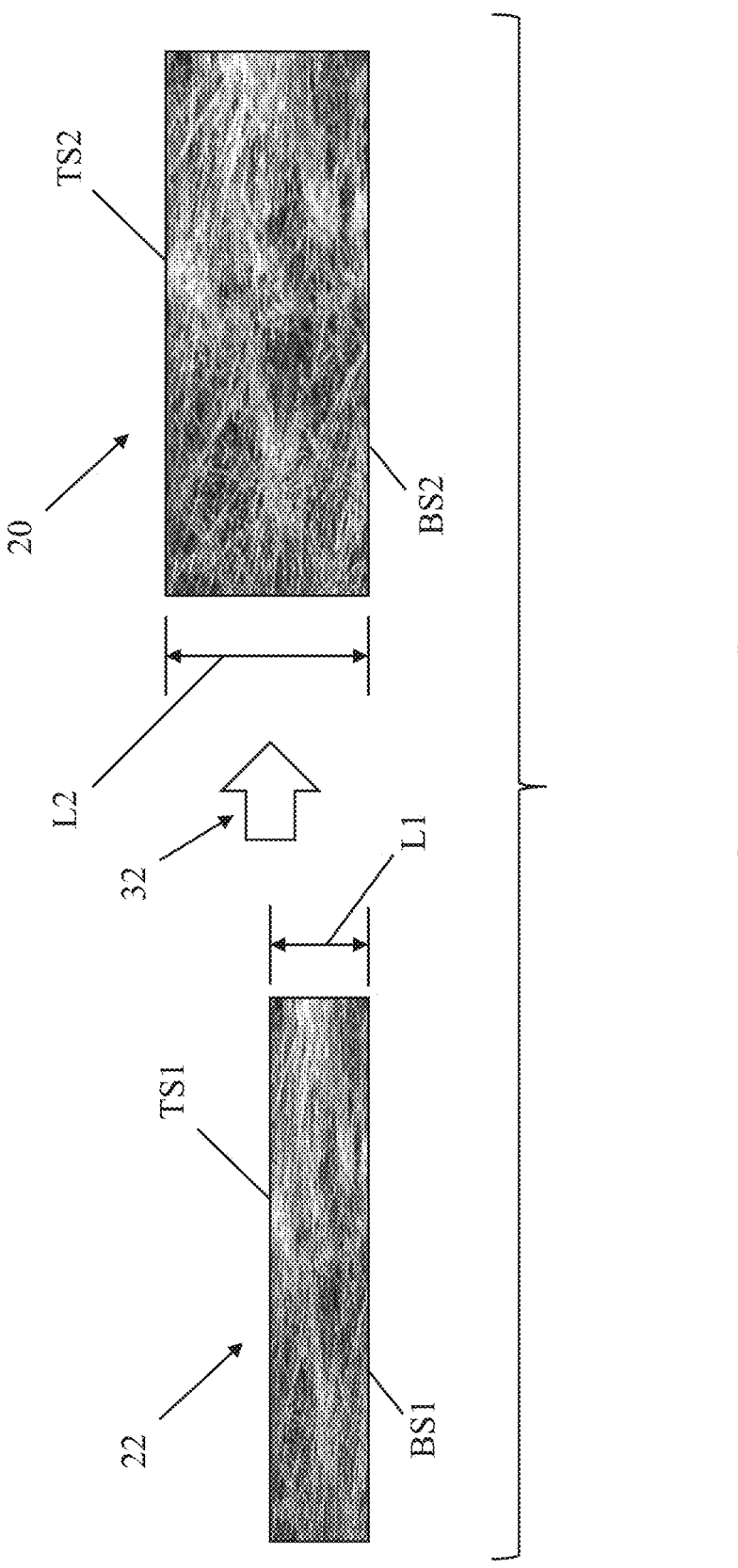
FIG. 4 is a cross-sectional representation of the unapertured non-woven precursor web and the hydro-enlarged apertured non-woven web of the present invention, showing the change in the loft from the unapertured non-woven precursor web to the hydro-enlarged apertured non-woven web as it passes through the hydro-enlarging station illustrated in FIG. 2.

FIG. 4 is a graphical illustration that is provided to highlight the increased loft imparted to the hydro-enlarged apertured non-woven web 20 as the unapertured non-woven precursor web 22 passes through the hydro-enlarging station 32.

Specifically, the unapertured non-woven precursor web 22 has an initial loft L1 before passing through the hydro-enlarging station 32. After passing through the hydro-enlarging station 32, the hydro-enlarged apertured non-woven web 20 has a final loft L2. The final loft L2 is greater than the initial loft L1.

The initial loft L1 is defined as the distance between a top surface TS1 (third surface) and a bottom surface BS1 (fourth surface) of the unapertured non-woven precursor web 22. Similarly, the final loft L2 is defined as the distance between a top surface TS2 (first surface) and a bottom surface BS2 (second surface) of the hydro-enlarged apertured non-woven web 20. The top surfaces TS1, TS2 and bottom surfaces BS1, BS2 are generally planar surfaces that are generally parallel to one another, respectively. It is noted that the apertures 44 may have a slightly conical shaped in the area immediately adjacent thereto. This conical shape may result from the pins 36 piercing through the non-woven web. Despite this slightly conical shape around the apertures 44, the surfaces are described as being planar to simplify the discussion of the present invention.

Figure 5:
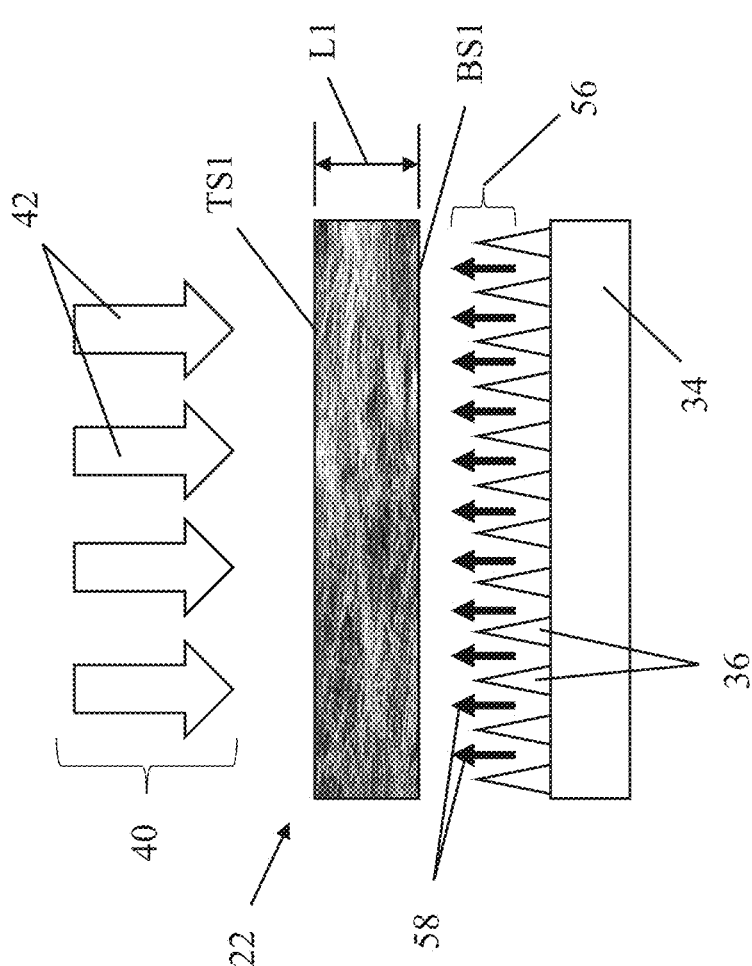
FIG. 5 is a cross-sectional, graphical illustration that helps to explain why it is believed that the loft of the unapertured nonwoven precursor web increases when the unapertured non-woven precursor web transitions to the hydro-enlarged apertured non-woven web.

FIG. 5 is a graphical illustration that assists with an explanation of why it is believed the loft increases from the initial loft L1 of the unapertured non-woven precursor web 22 to the final loft L2 of the hydro-enlarged apertured non-woven web 20.

As illustrated in FIG. 5, the pressurized stream 40 presses the unapertured non-woven precursor web 22 in the direction of the arrows 42, consistent with the illustration in FIG. 2. As discussed, the pressurized stream 40 creates the plurality of apertures 44 in the unapertured non-woven web precursor 22 to form the hydro-enlarged apertured non-woven web 20.

The pinned roller 34 has a solid surface. In other words, there are no openings in the pinned roller 34 to permit water/fluid from the pressurized stream 40 to pass through the pinned roller 34. As a result, at least a portion of the pressurized stream 40 rebounds, as a rebounded stream 56, from the pinned roller 34. The direction of the rebounded stream 56 is indicated by the arrows 58. Understandably, some of the rebounded stream 56 also will rebound from the surfaces of the pins 36, and, therefore, will not rebound in the same direction as the stream 56 rebounding from the pinned roller 34.

While not intending to be bound by theory, it is believed that the rebounded stream 56 pushes the fibers 28 apart, thereby increasing the loft from the initial loft L1 to the final loft L2. It is also contemplated that water/fluid rebounding from the surfaces of the pins 36 contributes to the expansion of the loft from the initial loft L1 to the final loft L2. In addition, it is believed that a layer of water/fluid develops in the spaces between the pins 36 that establishes a cushion space facilitating expansion of the unapertured non-woven precursor web 22 as it is processed through the hydro-enlarging station 32 to create the hydro-enlarged apertured non-woven web 20.

Several unapertured non-woven precursor webs 22 were examined in connection with the development of the hydro-enlarged apertured non-woven web 20 of the present invention. The following Table, Table 1, provides a comparison between the initial loft L1 and the final loft L2 for the non-woven webs that were examined.

Before discussing various parameters of the hydro-enlarged apertured non-woven web 20 that may be derived from Table 1, a brief overview is provided of the shapes and configurations of the pins employed to manufacture the tabulated examples of the hydro-enlarged apertured non-woven web 20 of the present invention.

Figures 6, 7, 8:
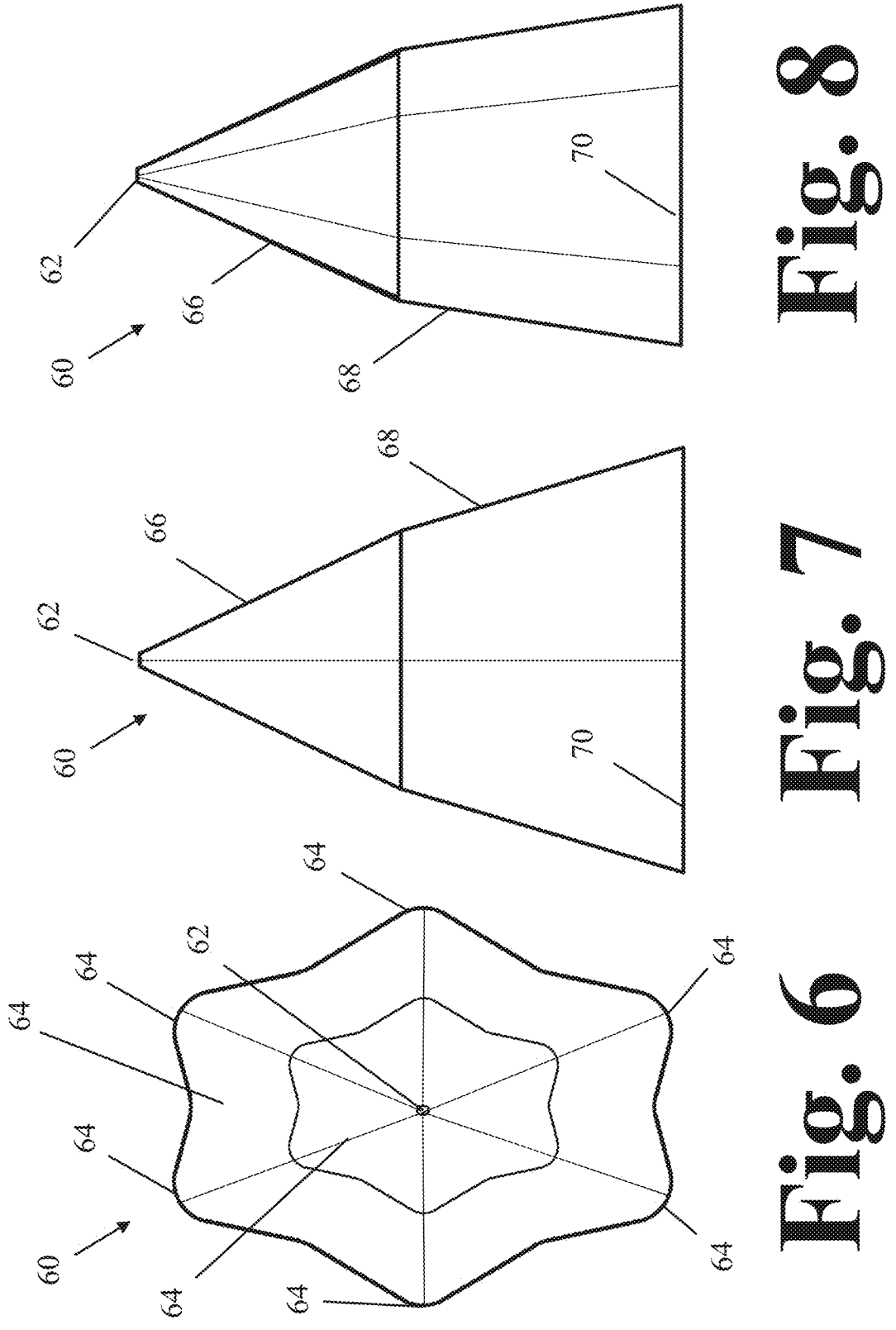
FIG. 6 is a graphical top view of a star-shaped pin that may be disposed on the pinned roller in the hydro-enlarging station to create the hydro-enlarged apertured non-woven web according to the present invention.
FIG. 7 is a graphical right side view of the pin illustrated in FIG. 6.
FIG. 8 is a graphical front view of the pin illustrated in FIG. 6.

FIGS. 6-8 illustrate a first embodiment of a pin 60 that may be disposed on the pinned roller 34. The pin 60 is referred to hereinafter as the star-shaped pin 60.

FIG. 6 is a top view of the star-shaped pin 60, illustrating that the star-shaped pin 60 has an apex 62 that is surrounded by six lobes 64, disposed in an elongated hexagram pattern. The star-shaped pin 60 also defines a top portion 66 and a bottom portion 68. The top portion 66 and the bottom portion 68 are distinguishable from one another in that the slope (slope=rise (height) (y-direction)/run (width) (x-direction)) of the sides of the top portion 66 is less than the slope of the sides of the bottom portion 68. In this fashion, the profile of the star-shaped pins 60 defines a bent pyramid.

FIG. 7 is a right side view of the star-shaped pin 60 illustrated in FIG. 6. As indicated above, the star-shaped pin

TABLE 1

| Sample Name | Basis Weight (gsm) | Initial Loft L1 (microns) | Final Loft L2 (microns) | Loft Increase (ΔL) | Water/ Fluid Pressure (psi/kPa) | Water/ Fluid Temp (° F./° C.) | Pin Details |
|---|---|---|---|---|---|---|---|
| Fitesa, Phobic Bico | 20 | 196 | 308 | 57% | 500/ 3447.4 | 125/ 51.67 | Pin Shape-Star, Pin Height-0.284", Pin Size at Base-0.221 (MD)/0.211 (TD), Pin Spacing-0.1838" (MD)/0.1686" (TD) |
| Fitesa, Phobic PP | 21 | 194 | 325 | 68% | 500/ 3447.4 | 116/ 46.67 | Pin Shape-Star, Pin Height-0.284", Pin Size at Base-0.221 (MD)/0.211 (TD), Pin Spacing-0.1838" (MD)/0.1686" (TD) |
| Hexadot Small SMS | 50 | 501 | 875 | 75% | 450/ 3102.6 | 115/ 46.11 | Pin Shape-Star, Pin Height-0.284", Pin Size at Base-0.221 (MD)/0.211 (TD), Pin Spacing-0.1838" (MD)/0.1686" (TD) |
| First Quality, FQN 10GSBO PHL-1000 | 10 | 103 | 174 | 69% | 450/ 3102.6 | 86/30 | Pin Shape-Round, Pin Height-0.2621", Pin Size at Base-0.110", Pin Spacing-0.1218" (MD)/0.2108" (TD) |
| First Quality, FQN 10GSBO PHL-1000 | 10 | 103 | 196 | 90% | 585/ 4033.4 | 89/ 31.67 | Pin Shape-Round, Pin Height-0.125", Pin Size at Base-0.055", Pin Spacing-0.0609" (MD)/0.1055" (TD) |
| First Quality, FQN 10GSBO PHL-1000 | 10 | 103 | 182 | 77% | 400/ 2757.9 | 84/ 28.89 | Pin Shape-Star, Pin Height-0.160", Pin Size at Base-0.111 (MD)/0.105 (TD), Pin Spacing-0.0924" (MD)/0.0842" (TD) |
| First Quality, N200SP B0002-735 | 20 | 228 | 371 | 63% | 550/ 3792.1 | 95/35 | Pin Shape-Round, Pin Height-0.2621", Pin Size at Base-0.110", Pin Spacing-0.1218" (MD)/0.2108" (TD) |
| First Quality, N200SP B0002-735 | 20 | 228 | 455 | 100% | 400/ 2757.9 | 101/ 38.33 | Pin Shape-Round, Pin Height-0.2621", Pin Size at Base-0.110", Pin Spacing-0.1218" (MD)/0.2108" (TD) |

60 takes the shape of a bent pyramid extending from the apex 62 to the base 70. The distance from the apex 62 to the base 70 defines the height of the star-shaped pin 60. As should be apparent, the left side view is a mirror image of the right side view.

FIG. 8 is a front view of the star-shaped pin 60 illustrated in FIG. 6. The rear view is a mirror image of the front view. It is noted that the profile of the star-shaped pin 60 is narrower from the front side than from the right side.

While the star-shaped pin 60 is illustrated with one configuration (as shown in FIGS. 6-9), it is noted that the present invention is not limited to the formation of a hydro-enlarged apertured non-woven web 20 using only star-shaped pins 60 with this configuration. The configuration of the star-shaped pin 60 may be varied without departing from the scope of the present invention.

To create the pinned roller 34 that is used to create the hydro-enlarged apertured non-woven web 20 of the present invention, the star-shaped pins 60 are secured to the surface of the pinned roller 34 in a conventional manner.

For example, it is contemplated that the surface of the pinned roller 34 will be manufactured with a plurality of the star-shaped pins 60 integrally formed thereon. Here, the pinned roller 34 may be machined to create the star-shaped pins 60.

It is also contemplated, however, that the star-shaped pins 60 may be manufactured separately and later secured to the surface of the pinned roller 34. The precise manner in which the pinned roller 34 is created is not critical to the present invention.

Figures 9, 10:
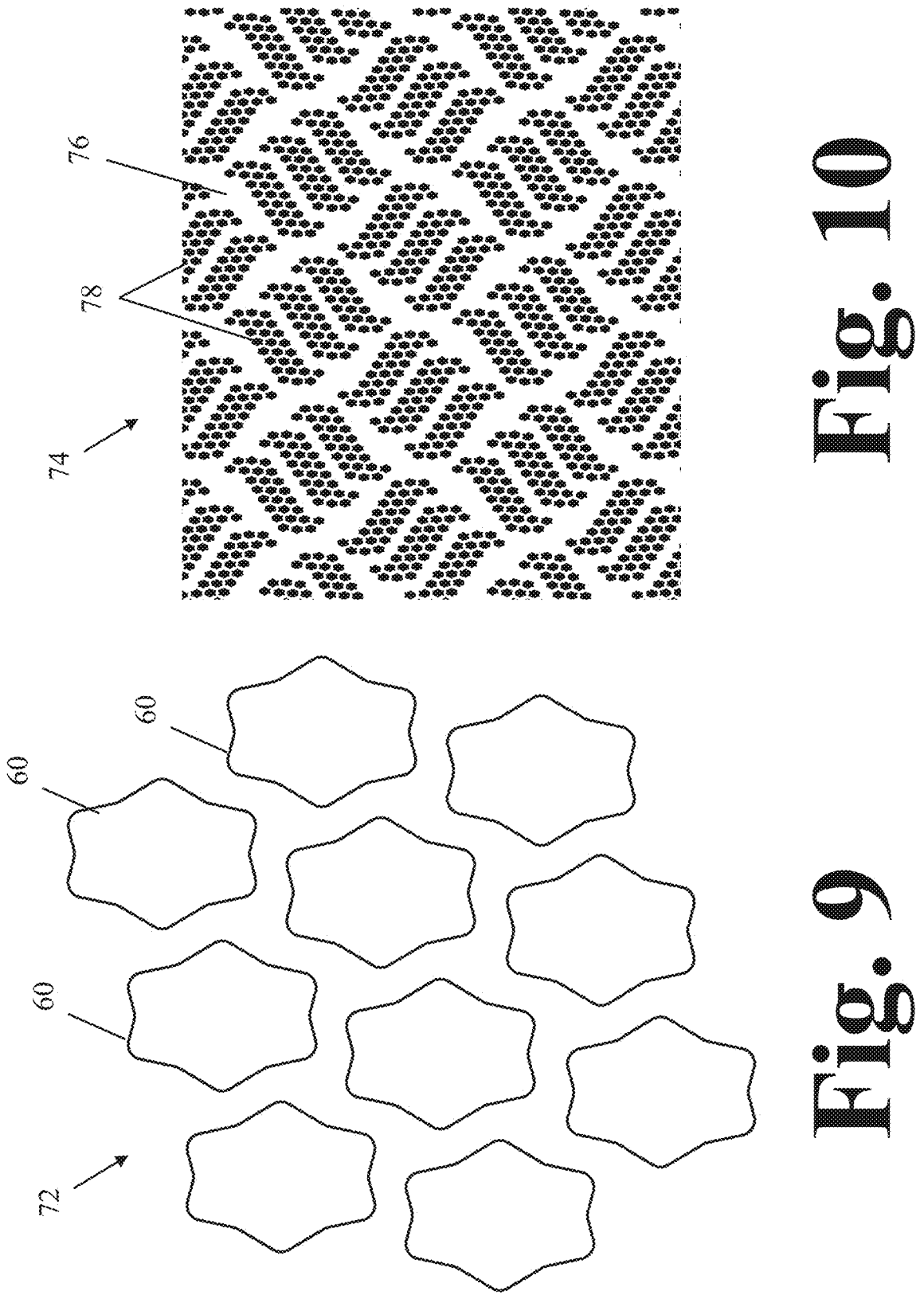
FIG. 9 is a graphical top view, illustrating a plurality of the star-shaped pins shown in FIG. 6, where the star-shaped pins are arranged in one contemplated pattern for creating the hydro-enlarged apertured non-woven web of the present invention.
FIG. 10 is a graphical, top view of one contemplated embodiment of a hydro-enlarged apertured non-woven web according to the present invention after having been pierced by the plurality of star-shaped pins illustrated, in part, in FIG. 9.

FIG. 9 is a top view of the surface of an embodiment of the pinned roller 34, showing one contemplated pattern 72 of a plurality of the star-shaped pins 60. As illustrated, the star-shaped pins 60 are arranged in a staggered pattern 72. As should be apparent to those skilled in the art, however, the star-shaped pins 60 may be arranged in any pattern, as required or as desired, without departing from the scope of the present invention.

FIG. 10 is a graphical, top view of one contemplated embodiment of the hydro-enlarged apertured non-woven web 20 of the present invention. Specifically, the hydro-enlarged apertured non-woven web 74 is understood to be formed from a pattern 76 comprising a plurality of star-shaped pins 60 arranged in groups 78 that are wave-like in shape and distribution. Again, this pattern 76 is merely exemplary of the wide variety of patterns that may be employed without departing from the scope of the present invention. As may be apparent, the pattern 72 illustrated in FIG. 9 is a subset of the pattern 76 illustrated in FIG. 10.

Figures 11, 12, 13:
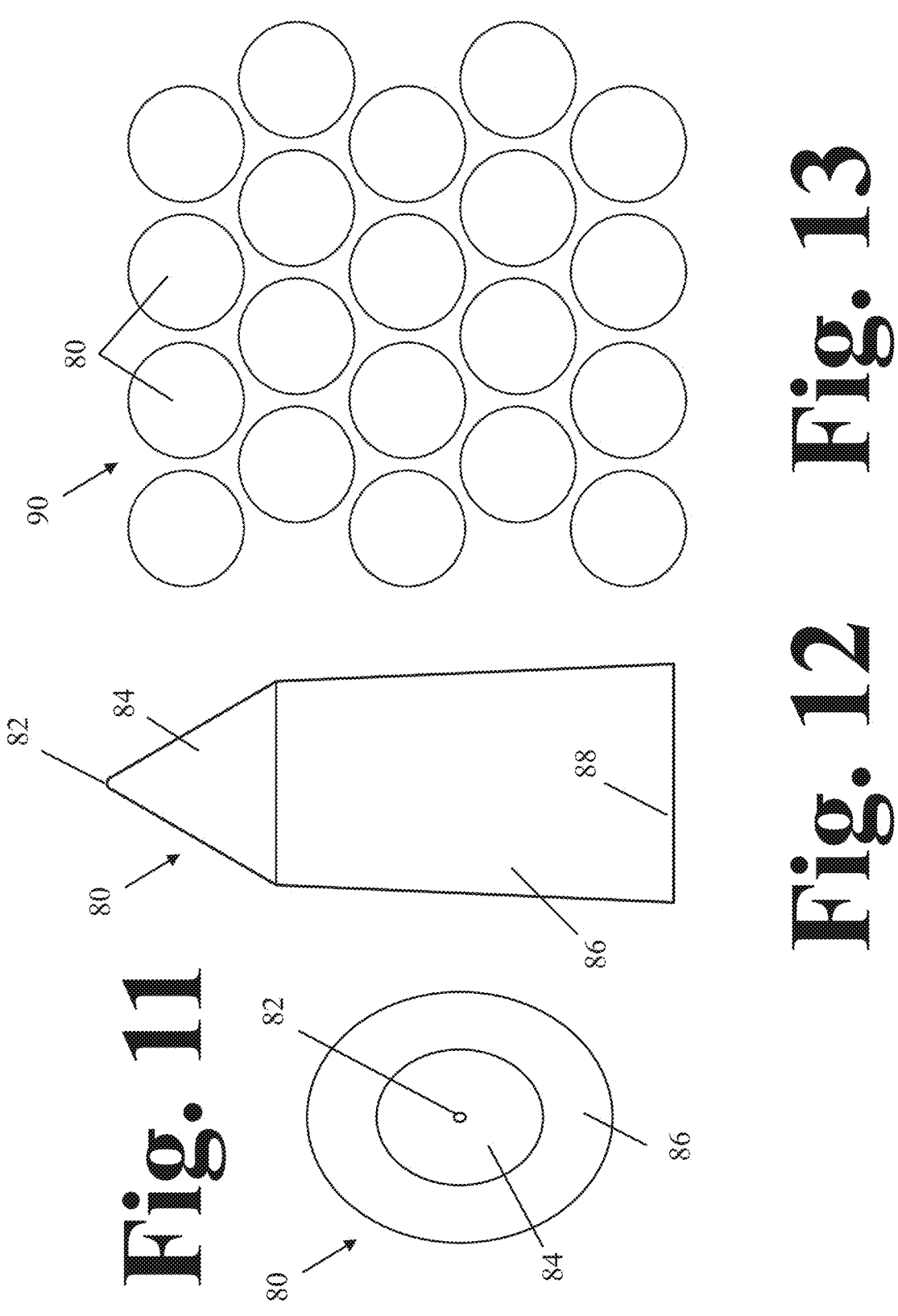
FIG. 11 is a top view of a round pin, which may be disposed on the pinned roller in the hydro-enlarging station to create the hydro-enlarged apertured non-woven web according to the present invention.
FIG. 12 is a side view of the round pin illustrated in FIG. 11.
FIG. 13 is a graphical, top view of one contemplated arrangement of a plurality of the round pins illustrated in FIG. 11, showing a pattern contemplated for the round pins on the pinned roller illustrated in FIG. 2.

FIG. 11 is a top view of a round pin 80. The round pin 80 has an apex 82. The round pin 80 defines a top portion 84 and a bottom portion 86. The top portion 84 and the bottom portion 86 are distinguishable from one another in that the slope of the sides of the top portion 84 is less than the slope of the sides of the bottom portion 86. In this fashion, the profile of the round pins 80 defines a conical obelisk.

FIG. 12 is a side view of the round pin 80 illustrated in FIG. 11. As indicated above, the round pin 80 takes the shape of a conical obelisk extending from the apex 82 to the base 88. The distance from the apex 82 to the base 88 defines the height of the round pin 80.

FIG. 13 is a top view of the surface of an embodiment of the pinned roller 34, showing one contemplated pattern 90 of a plurality of the round pins 80. As illustrated, the round pins 80 are arranged in a staggered pattern 90. As should be apparent to those skilled in the art, however, the round pins 80 may be arranged in any pattern, as required or as desired, without departing from the scope of the present invention.

As should be apparent from the foregoing, the pins, regardless of their shapes, may be arranged in any desirable pattern on the pinned roller 34 to create an aperture pattern in the hydro-enlarged apertured non-woven web 20 as required or desired.

Returning to the data provided in Table 1, several unapertured non-woven precursor webs 22 were examined. The unapertured non-woven precursor webs 22 are listed according to their sample names and basis weights, as tabulated in Table 1.

Using the Phobic Bico sample, manufactured by Fitesa Nonwovens, as an example, the information provided in Table 1 is now described. In particular, the Phobic Bico sample, manufactured by Fitesa Nonwovens, is reported as having a basis weight of 20 gsm. The initial loft L1 of the unapertured non-woven precursor web 22 is provided as 196 microns, as measured using standard techniques know to those skilled in the art. After being processed by the hydro-enlarging station 32, the hydro-enlarged apertured non-woven web 20 has a final loft L2 of 308 microns. This is a net increase in loft of 57%. These same conventions may be employed to evaluate the data for the remaining samples listed in Table 1.

Table 1 also reports that the Phobic Bico, manufactured by Fitesa Nonwovens, was subjected to a water pressure (the predetermined water pressure) of 500 psi. The water temperature (the predetermined water temperature) was 125° F. In addition, as noted in Table 1, the star-shaped pins 60 were employed to create the hydro-enlarged apertured non-woven web 20. The star-shaped pins 60 had a height of 0.284 inches. The star-shaped pins had a size, at the base 70, of 0.22 inches in the machine direction MD and 0.21 inches in the transverse direction TD. The pins were spaced from one another by a distance of 0.1838 inches in the machine direction MD and 0.1686 inches in the transverse direction TD.

The water pressure utilized for each of the samples reported in Table 1 was within a range of 400-585 psi (2757.9-4033.4 kPa). From this data, for one embodiment of the present invention, it is contemplated that the water pressure to be applied to the unapertured non-woven precursor web 22 to create the hydro-enlarged apertured non-woven web 20 will be selected within a range of 250-650 psi (1723.7-4481.6 kPa). In another contemplated embodiment, the water pressure is selected to fall within a range of 400-550 psi (2757.9-3792.1 kPa. Specific water pressures that may be employed include, but are not limited to, 350 psi (2413.2 kPa), 400 psi (2757.9 kPa), 450 psi (3102.6 kPa), 500 psi (3447.4 kPa), 550 psi (3792.1 kPa), 585 psi (4033.4 kPa), 600 psi (4136.9 kPa), and 650 psi (4481.6 kPa).

The water temperature utilized for each of the samples reported in Table 1 was within a range of 84-125° F. (28.89° C.-51.67° C.). From this data, it is contemplated that the water temperature to be applied to the unapertured non-woven precursor web 22 to create the hydro-enlarged apertured non-woven web 20 will be selected within a range of 75-140° F. (23.89-60° C.). Still further, the water/fluid temperature may be selected to fall within a range of 100-125° F. (37.78-51.67° C.). Specific water/fluid temperatures that may be employed include, but are not limited to, 75° F. (23.89° C.), 80° F. (26.67° C.), 84° F. (28.89° C.), 85° F. (29.44° C.), 86° F. (30° C.), 89° F. (31.67° C.), 90° F. (32.22° C.), 95° F. (35° C.), 100° F. (37.78° C.), 101° F. (38.33° C.), 105° F. (40.56° C.), 110° F. (43.33° C.), 115° F.

(46.11° C.), 116° F. (46.67° C.), 120° F. (48.89° C.), 125° F. (51.67° C.), 130° F. (54.44° C.), 135° F. (57.22° C.), and 140° F. (60° C.).

While water was used in the reported examples, any other may be substituted for water. In other words, the invention is not limited to water, but encompasses any fluids more broadly.

As identified in Table 1, the initial loft L1 is contemplated to fall within a range of 50-600 microns. Still further, the initial loft L1 may fall within a range of 100-500 microns. Specific examples of the initial loft L1 include, but are not limited to 100, 200, 225, or 500 microns.

As also identified in Table 1, the final loft L2 is contemplated to fall within a range of 150-1000 microns. Still further, the final loft L2 may fall within a range of 200-900 microns. Specific examples of the final loft L2 include, but are not limited to 200, 325, 450, or 875 microns.

As is apparent from Table 1, the loft increase $\Delta L$ is calculated as a percentage according to the equation $\Delta L = [(L2-L1)/L1]*100$. The loft increase $\Delta L$ falls within a range of 57-100%. From this data, it is contemplated that the loft increase $\Delta L$ for non-woven webs will fall within a range between 50-110%. Other ranges for the loft increase $\Delta L$ include 60-90% and 70-80%. The loft increase $\Delta L$ includes, but is not limited to any one of the following specific loft increases: 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, and 110%.

For purposes of the present invention, as discussed hereinabove, the loft increase $\Delta L$ contributes to the soft feel of the hydro-enlarged apertured non-woven web 20 of the present invention. The loft increase $\Delta L$ results from the application of pressurized streams 40 to the unapertured non-woven precursor web 22 in the hydro-enlarging station 32, as described above.

Figures 14, 15:
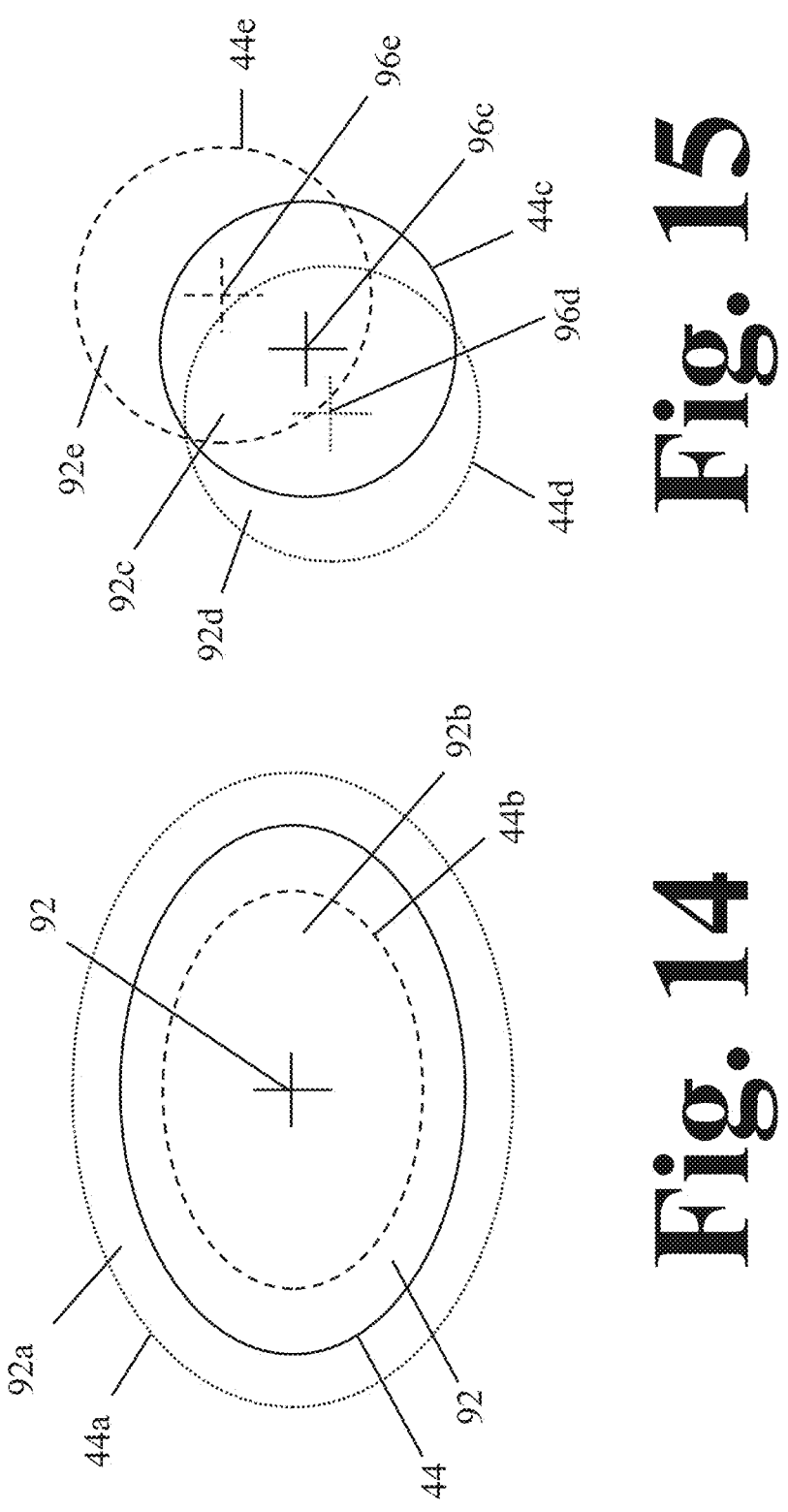
FIG. 14 is a graphical illustration of one aspect of the present invention, showing the areal randomness of the apertures in the hydro-enlarged apertured non-woven web of the present invention.
FIG. 15 is a graphical illustration of another aspect of the present invention, showing the positional randomness of the apertures in the hydro-enlarged apertured non-woven web of the present invention.

FIGS. 14 and 15 are graphical representations of further aspects of the present invention. Specifically, FIGS. 14 and 15 illustrate aspects of randomness that are introduced at the hydro-enlarging station 32 when the pressurized stream 40 is applied to the unapertured non-woven precursor web 22.

"Randomness" refers to the creation of apertures 44 that are not uniform across the surface of the hydro-enlarged apertured non-woven web 20. In particular, when the apertures 44 are formed, each aperture 44 may have an open area 92 with a different size even though each of the pins, such as the star-shaped pins 60, are of identical dimension. This aspect of randomness is discussed in connection with FIG. 14. Still further, each aperture 44 may not be located at a position that established a precisely uniform pattern of the apertures 44. This aspect of randomness is discussed in connection with FIG. 15.

In FIG. 14, the apertures 44 are illustrated as ellipses. In FIG. 15, the apertures 44 are illustrated as circles. It is noted that the use of ellipses and circles is merely to simplify the discussion that follows. As indicated by FIG. 3, the apertures 44 may have any shape without departing from the scope of the present invention.

FIG. 14 illustrates a first aspect of randomness. In particular, FIG. 14 illustrates the concept of areal randomness, which encompasses deviations in the open area 92 for each of the apertures 44. It is noted that, in the prior art, such as in the hot pin apertured non-woven web 10 illustrated in FIG. 1, the apertures 12 are all the same size, meaning that they have the same open area.

The open area 92 illustrated in FIG. 14 constitutes the "ideal" open area 92 for each aperture 44 if each aperture 44 were exactly the same as each and every other aperture 44 in the hydro-enlarged apertured non-woven web 20.

In the present invention, however, the hydro-enlarging station 32 introduces areal randomness into the open areas 92 of the apertures 44. As a result, some of the apertures 44a have a larger open area 92a than the ideal open area 92. Other apertures 44b have an open area 92b that is smaller than the ideal open area 92.

For purposes of the present invention, it is contemplated that the areal difference from the ideal open area 92 will be within a range of ±20%. As such, if the ideal open area 92 is set at 10 $\mu m^2$, the apertures 44 in the hydro-enlarged apertured non-woven web 20 will have apertures 44 having open areas from 8-12 $\mu m^2$. In still another embodiment, the areal difference is ±15%. Still further, the areal difference may be ±10%. Other areal differences include, but are not limited to ±9%, ±8%, ±7%, ±6%, 5%, ±4%, ±3%, ±2%, or ±1%. As a reference, a common center point 94 is illustrated for each of the apertures 44, 44a, and 44b.

FIG. 15 illustrates a second aspect of randomness. In particular, FIG. 15 illustrates the concept of positional randomness, which encompasses deviations in the positional location 96 for each of the apertures 44. It is noted that, in the prior art, such as in the hot pin apertured non-woven web 10 illustrated in FIG. 1, the apertures 12 all share the same positional relationship. In other words, the center point for each aperture 12 is located at the same distance from each and every other center point of each and every other aperture 12.

In FIG. 15, it is noted that the open areas 92c, 92d, 92e for each of the apertures 44c, 44d, 44e are identical. Moreover, it is noted that aperture 44c has a center point 96c that is considered to be the ideal center point location, consistent with the prior art.

In the present invention, in addition to areal randomness, the hydro-enlarging station 32 introduces positional randomness into the locations of the apertures 44. As a result, some of the apertures 44d, 44e have center points 96d, 96e that deviate from the ideal center point location 92c.

For purposes of the present invention, it is contemplated that the positional difference from the ideal center point location 96c will be within a range of ±20%. In still another embodiment, the positional difference is ±15%. Still further, the positional difference may be ±10%. Other positional differences include, but are not limited to ±9%, ±8%, ±7%, ±6%, ±5%, ±4%, ±3%, ±2%, or ±1%.

While not being bound to theory, it is believed that the areal difference and the positional difference introduced by the hydro-enlarging station 32 depends on a number of factors. In particular, the pressurized streams 40 are contemplated to bounce off of the pins 36 in various directions, causing the fibers 28 to be more randomly distributed than in the prior art. The direction(s) of the pressurized streams 40, the water/fluid pressure, the water/fluid temperature, and the speed of the unapertured non-woven precursor web 22 through the hydro-enlarging station 32 are some of the factors that are believed to contribute to both the areal randomness and the positional randomness of the apertures 44. Other possible factors include the number, density, and locations of the bond points in the non-woven precursor web.

As noted above, the unapertured non-woven precursor web 22 is contemplated to be made from a polymer that includes, but is not limited to, polyethylene, polypropylene, elastomers, polyesters, rayon, cellulose, nylon, and blends thereof.

In an alternative embodiment, it is contemplated that the unapertured non-woven precursor web 22 may be made from polylactic acid or polyactide ("PLA"). In one definition, PLA is known to be a biodegradable and bioactive polyester made up of lactic acid building blocks. PLA may be derived from renewable sources including, but not limited to cornstarch, cassava roots, chips, starch, and sugarcane, among others. The properties of PLA polymers range from amorphous glassy polymers to semi-crystalline polymers and highly crystalline polymers with a glass transition temperature of about 60-65° C., a melting temperature of about 130-180° C., and a Young's modulus of about 2.7-16 GPa. It is noted that these aspects of PLA are not intended to be limiting of the present invention but are provided merely to identify known properties of the material.

As should be apparent to those skilled in the art, one aspect of PLA is that the material tens to absorb water. In addition, fibers made from PLA polymers tend to be fragile. This means that fibers 28 made from PLA have a tendency both to swell and to break apart when subjected to hydraulic forces and stresses, such as those imposed during hydro-enlargement.

Those skilled in the art, therefore, traditionally avoided PLA polymers when processing an unapertured non-woven precursor web 22, especially in an environment, as here, where the unapertured non-woven precursor web 22 would be subjected to high-pressure processing involving water. Simply, those skilled in the art expected that any unapertured non-woven precursor web 22 made from PLA, if subjected to the stresses attendant to hydro-enlargement, would be shredded and/or destroyed. As such, the resulting hydro-enlarged apertured non-woven web 20 would not be useable in any capacity. For this reason, among others, PLA polymers traditionally have been avoided.

However, as noted above, because PLA is a polymer that is derivable from renewable resources, PLA is an attractive polymer for the creation of disposable products such as absorptive devices into which the present invention might be incorporated (i.e., feminine hygiene products, diapers, and the like). PLA materials also are known to have improved biodegradability parameters by comparison with petrochemical-based plastics.

In connection with the present invention, a 25 gsm unapertured non-woven precursor web 22 having an average thickness of about 131 microns (0.005 inch) and an average air permeability of about 193 $m^3/m^2/min$ (632.9 $ft^3/ft^2/min$) was hydro-enlarged at a water pressure of 300 psi (206.4 kPa) and a temperature of 160° F. (71.11° C.) using oval-shaped pins to create the hydro-enlarged apertured non-woven web 20.

In this example, the hydro-enlarged apertured non-woven web 20 displayed a final loft L2 of 201 microns (0.008 inch) and a final air permeability of 301 $m^3/m^2/min$ (987.1 $ft^3/ft^2/min$). Thus, the hydro-enlarged apertured non-woven web 20 had final loft L2 that was 1.53 times greater (53% greater) than the initial loft L1. The final air permeability was 1.56 times greater (56% greater) than the initial air permeability.

In connection with this example, it is noted that air permeability also may be an attractive feature associated with the hydro-enlarged apertured non-woven web 20, because it is an indicator of how permeable the hydro-enlarged apertured non-woven web 20 is to fluids. Air permeability, which may be measured by a device such as a Textest FX3300 Air Permeability Tester, measures the flowability of air through a material.

In this example, the unapertured non-woven precursor web 22 included fibers 28 made from a bicomponent polyethylene/PLA material with a composition of 50% polyethylene and 50% PLA.

As noted above, those skilled in the art would not have expected a PLA material or a PLA-containing material to survive the hydro-enlarging process. As a result, those skilled in the art would not have subjected a PLA-containing material to hydro-enlarging.

Surprisingly, the PLA-containing material not only survived the hydro-enlarging process, but it did so in a manner such that the hydro-enlarged apertured non-woven web 20 exhibits properties superior to those in the prior art. In other words, these PLA-containing material satisfied the parameters set forth herein for the present invention. These results were not expected.

For purposes of the present invention, a 50/50 bicomponent PE/PLA material is but one example of a bicomponent PE/PLA material that may be employed. It is contemplated that the ratio of PE to PLA may fall within a wide range without departing from the scope of the present invention. In particular, it is contemplated that the ratio of PE to PLA may vary from a 20/80 ratio to an 80/20 ratio, with any specific ratio in between satisfying the present invention. Even more specifically, without surrendering any fractional ratio between the values listed, the following PE/PLA ratios are contemplated to fall within the scope of the present invention (PE/PLA): 20/80, 21/79, 22/78, 23/77, 24/76, 25/75, 26/74, 27/73, 28/72, 29/71, 30/70, 31/69, 32/68, 33/67, 34/66, 35/65, 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, and 80/20.

In addition, it is contemplated that other polymers may be employed instead of polyethylene for the bicomponent PE/PLA material. For example, the polymer may be polyethylene, polypropylene, elastomers, polyesters, rayon, cellulose, nylon, and blends of these polymers, without departing from the scope of the present invention. In one contemplated embodiment of the bicomponent PE/PLA material (or any variant thereof), the PE component (or the alternative to the PE component) may form at least a partial sheath around fibers made from the PLA material, as should be apparent to those skilled in the art.

The ratio of polymer to PLA is contemplated to be the same as enumerated hereinabove. Specifically, the following polymer/PLA ratios also are contemplated to be between 20/80 and 80/20. As enumerated above, without surrendering any fractional ratio between the values listed, the following polymer/PLA ratios are contemplated to fall within the scope of the present invention (polymer/PLA): 20/80, 21/79, 22/78, 23/77, 24/76, 25/75, 26/74, 27/73, 28/72, 29/71, 30/70, 31/69, 32/68, 33/67, 34/66, 35/65, 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, and 80/20.

As discussed in connection with prior embodiments, it is also contemplated that the bicomponent polymer/PLA material may incorporate a surfactant. The surfactant may be mixed into the bicomponent polymer/PLA material and/or coated thereon, as discussed in connection with other embodiments of the present invention.

As should be apparent from the foregoing, where employed, the hydro-enlarged apertured non-woven web 20 made from the polymer/PLA bicomponent material is contemplated to be manufactured according to the methods and apparatuses described hereinabove. The hydro-enlarged apertured non-woven web 20 made from the polymer/PLA bicomponent material also is contemplated to exhibit properties consistent with those listed and discussed above in connection with Table 1.

As discussed hereinabove, the embodiments of the present invention are exemplary only and are not intended to limit the present invention. Features from one embodiment are interchangeable with other embodiments, as should be apparent to those skilled in the art. As such, variations and equivalents of the embodiments described herein are intended to fall within the scope of the claims appended hereto.

What is claimed is:

1. A hydro-enlarged apertured non-woven web, comprising:
   a plurality of fibers;
   a plurality of bond points securing the plurality of fibers to one another to define a non-woven web;
   a first surface defining a planar top to the non-woven web;
   a second surface defining a planar bottom to the non-woven web;
   wherein the second surface is separated from the first surface by a first distance defining a loft;
   a plurality of apertures extending through the non-woven web from the first surface to the second surface;
   wherein the plurality of apertures is formed by spraying a fluid against an unapertured precursor web, causing a plurality of pins disposed on a pinned roller to punch through the unapertured precursor web;
   wherein the unapertured precursor web has a third surface defining a planar top;
   wherein the unapertured precursor web has a fourth surface defining a planar bottom;
   wherein the third surface is separated from the fourth surface by a second distance defining a precursor loft;
   wherein the loft is greater than the precursor loft by a loft increase within a range of 50-110%.

2. The hydro-enlarged apertured non-woven web of claim 1, wherein the non-woven web has a basis weigh in a range of 8-100 gsm.

3. The hydro-enlarged apertured non-woven web of claim 2, wherein the non-woven web has a basis weight in a range of 10-60 gsm.

4. The hydro-enlarged apertured non-woven web of claim 3, wherein the non-woven web has a basis weight of one of 10 gsm, 20 gsm, or 50 gsm.

5. The hydro-enlarged apertured non-woven web of claim 1, wherein the loft is in a range of 150-1000 microns.

6. The hydro-enlarged apertured non-woven web of claim 5, wherein the loft is in a range of 200-900 microns.

7. The hydro-enlarged apertured non-woven web of claim 6, wherein the loft is in at least one of 200, 325, 450, or 875 microns.

8. The hydro-enlarged apertured non-woven web of claim 1, wherein the precursor loft is in a range of 50-600 microns.

9. The hydro-enlarged apertured non-woven web of claim 8, wherein the precursor loft is in a range of 100-500 microns.

10. The hydro-enlarged apertured non-woven web of claim 8, wherein the precursor loft is one of 100, 200, 225, or 500 microns.

11. The hydro-enlarged apertured non-woven web of claim 1, wherein the loft increase is within a range of 60-90%.

12. The hydro-enlarged apertured non-woven web of claim 11, wherein the loft increase is within a range of 70-80%.

13. A method of manufacturing a hydro-enlarged apertured non-woven web, comprising:
   introducing an unapertured non-woven precursor web to a pinned roller comprising a surface on which a plurality pins are disposed;
   wherein the unapertured non-woven precursor web comprises a plurality of fibers secured to one another at a plurality of bond points;
   wherein the unapertured non-woven precursor web has a first surface defining a planar top and a second surface defining a planar bottom;
   wherein the second surface is separated from the first surface by a first distance defining a precursor loft;
   spraying pressurized fluid against the first surface, thereby causing a plurality of pins disposed on a pinned roller to punch through the unapertured non-woven precursor web to create a plurality of apertures therethrough extending through the unapertured non-woven precursor web from the first surface to the second surface, resulting in the hydro-enlarged apertured non-woven web;
   wherein the hydro-enlarged apertured non-woven web has a third surface defining a planar top and a fourth surface defining a planar bottom;
   wherein the third surface is separated from the fourth surface by a second distance defining a loft;
   wherein the spraying causes the loft to be greater than the precursor loft; and
   wherein the loft is greater than the precursor loft by a loft increase within a range of 50-110%.

14. The method of claim 13, wherein the pressurized fluid is pressurized within a range from 350-650 psi (2413.2-4481.6 kPa).

15. The method of claim 14, wherein the pressurized fluid is pressurized within a range from 400-550 psi (2757.9-3792.1 kPa).

16. The method of claim 15, wherein the pressurized fluid is pressurized to one of 400 psi (2757.9 kPa), 450 psi (3102.6 kPa), 500 psi (3447.4 kPa), or 585 psi (4033.4 kPa).

17. The method of claim 13, wherein the pressurized fluid is maintained at a temperature within a range of 75-140° F. (23.89-60° C.).

18. The method of claim 17, wherein the pressurized fluid is maintained at a temperature within a range of 100-125° F. (37.78-51.67° C.).

19. The method of claim 18, wherein the pressurized fluid maintained at a temperature of one of 101° F. (38.33° C.), 115° F. (46.11° C.), 116° F. (46.67° C.), or 125° F. (51.67° C.).

20. The method of claim 13, wherein the loft increase is within a range of 60-90%.

21. The method of claim 20, wherein the loft increase is within a range of 70-80%.

* * * * *